(12) United States Patent
Kulik et al.

(10) Patent No.: US 8,983,028 B2
(45) Date of Patent: Mar. 17, 2015

(54) DENSITY PROFILE MEASUREMENT BY DETECTING BACKSCATTERED RADIATION WITH POSITION-SENSITIVE DETECTOR

(75) Inventors: Alex Kulik, Sugar Land, TX (US); Alexander Joseph Esin, Sugar Land, TX (US); Nikolay Baturin, Sugar Land, TX (US); Soovo Sen, Houston, TX (US); Michael George Brosseau, Stafford, TX (US)

(73) Assignee: Thermo Fisher Scientific Inc., Sugarland, TX (US)

( * ) Notice: Subject to any disclaimer, the term of this patent is extended or adjusted under 35 U.S.C. 154(b) by 688 days.

(21) Appl. No.: 13/298,155

(22) Filed: Nov. 16, 2011

(65) Prior Publication Data

US 2013/0123990 A1 May 16, 2013

(51) Int. Cl.
G01N 23/02 (2006.01)
G01N 9/24 (2006.01)

(52) U.S. Cl.
CPC .................. *G01N 9/24* (2013.01)
USPC ........................................ 378/59; 378/89

(58) Field of Classification Search
USPC ................................. 378/57, 58, 89
See application file for complete search history.

(56) References Cited

U.S. PATENT DOCUMENTS

| | | | |
|---|---|---|---|
| 4,197,462 A | 4/1980 | Kopp | |
| 4,266,425 A | 5/1981 | Allport | |
| 5,864,600 A | 1/1999 | Gray et al. | |
| 6,879,425 B2 | 4/2005 | Damm et al. | |
| 7,469,033 B2 | 12/2008 | Kulik et al. | |
| 2003/0072413 A1 | 4/2003 | Yokhin et al. | |
| 2008/0226026 A1* | 9/2008 | Kulik et al. | 378/52 |
| 2010/0025592 A1* | 2/2010 | Tumer | 250/370.08 |

FOREIGN PATENT DOCUMENTS

| | | |
|---|---|---|
| DE | 2461877 A1 | 7/1976 |
| DE | 102009012233 A1 | 9/2010 |
| EP | 1921435 A2 | 5/2008 |
| GB | 898799 A | 6/1962 |
| GB | 923630 A | 4/1963 |
| GB | 2482606 A | 2/2012 |
| WO | 03021234 A1 | 3/2003 |

OTHER PUBLICATIONS

Combined Search and Examination Report under Sections 17 and 18(3) issued Feb. 8, 2013 in corresponding United Kingdom application No. GB1220502.7 (7 pages).
First Office Action (w/translation) issued Apr. 8, 2014 in corresponding German application No. 102012022526.1 (10 pages).
First Office Action (w/translation) issued Jul. 3, 2014 in corresponding Chinese application No. 201210465004.8 (21 pages).

* cited by examiner

*Primary Examiner* — Hoon Song
(74) *Attorney, Agent, or Firm* — Osha · Liang LLP

(57) ABSTRACT

A method for measuring a density profile of a fluid in a process vessel is disclosed. The method includes emitting gamma rays into the fluid and acquiring a backscattered gamma ray counts distribution using at least one position sensitive gamma ray detector disposed proximate the vessel. The method further includes determining the density profile of the fluid contained in the process vessel based on the backscattered gamma ray counts distribution.

18 Claims, 11 Drawing Sheets

DENSITY PROFILE MEASUREMENT BY DETECTING BACKSCATTERED RADIATION WITH POSITION-SENSITIVE DETECTOR

BACKGROUND

Gamma rays have been used to measure the density and level of fluids in a vessel by using a gamma-ray source positioned opposite a gamma-ray detector. These through-transmission gamma-ray density and level measurements are useful where the materials measured are hazardous, extremely hot, or where direct contact measurements are otherwise not possible. Additionally, the source and detector are mounted outside the vessel, and no modification to the vessel is required. Gamma rays emitted by a source may be absorbed or attenuated by the vessel and the material in the vessel. The strength of the gamma radiation reaching a detector opposite the source may be used to indicate the density or level of a fluid in a vessel based upon the intensity of the source.

When measuring fluid level, for example, multiple gamma-ray emitters and/or detectors may be positioned at opposite sides of a vessel, where the presence or absence of a signal (or a nominal low signal) may indicate the presence or absence of a fluid in place between the source and detector. The size of a vessel in a signal/no signal level detector may be much larger than that for a gamma-ray densitometer, as described below, as gamma rays are not as readily absorbed or attenuated by vapors in the vessel.

With respect to fluid density, for example, fluid passing between the gamma-ray source and detector may absorb or attenuate gamma rays emitted by the source. A high radiation count indicates a low fluid density while a low count indicates high fluid density.

However, through-transmission density measurement using gamma rays is viable only for limited vessel sizes and/or fluid densities. For example, for a similar sized source, at higher fluid densities, the fluid may absorb more gamma rays, thus resulting in fewer gamma rays reaching the detector. Similarly, as vessel size is increased, gamma rays must pass through a greater quantity of material (vessel and fluid) absorbing the gamma rays, resulting in fewer gamma rays reaching the detector. Therefore, gamma-ray density measurements in this manner are currently only viable for vessels up to about 1 meter in diameter.

Another disadvantage in the present use of gamma rays for through-transmission density measurements is that the solid angle subtended by a fixed size detector, and thus the counting rate, scales inversely with the size of the vessel squared. The counting rate n may be approximated by the equation:

$$n \sim \Omega e^{-d/\lambda} \sim (e^{-d/\lambda})/d^2 \quad (1)$$

where n is the counting rate, d is the vessel diameter, and $\lambda$ is the absorption length, which depends on density. For a fixed sized detector, an increase in the vessel diameter d results in a lower count rate and a greater rate of error. Accordingly, for large vessels in noisy environments, it may become impossible to distinguish the gamma ray signal from the spurious background signal and, thus, useful information cannot be extracted.

To overcome the thickness, size, and density limitations, the intensity of the gamma-ray source may be increased, thus resulting in a measurable quantity of gamma rays reaching the detector. However, cost, safety, multi-unit effectiveness, and security may each limit the source intensity that may be used. For example, the use of a radioactive source creates personnel safety and environmental concerns and requires lead or tungsten shielding to protect personnel, special handling precautions and equipment, as well as disposal and remediation procedures. Furthermore, because gamma rays are produced from a point source and not a directional source, as the size of the source increases, the amount of shielding required to contain the radiation in directions other than through the vessel must be increased, thus, adding further to the cost.

With respect to multi-unit effectiveness, a chemical plant may desire to use gamma-ray level and density gauges on multiple vessels. However, as the number of gauges is increased or the intensity of gamma-ray sources is increased to overcome size limitations, cross-talk between gamma-ray sources and detectors on adjacent vessels may occur, resulting in decreased effectiveness and potentially erroneous readings.

With respect to the problem of measuring a density profile, i.e., the density as a function of elevation in a vessel, similar problems arise. For example, when attempting to use multiple units on a single vessel in order to estimate density profiles of the fluid contained in the vessel, size limitations and cross-talk between gamma-ray sources make existing technology incapable of producing accurate and reliable density profile measurements.

Regarding security, due to growing worldwide concerns about the proliferation and possible smuggling or other transport of radioactive materials, state, local, and national governments regulate facility security requirements based upon the total amount of radioactive material that may be present at a single site. For example, the State of Texas requires additional security measures (e.g., background checks, accessibility, etc.) at facilities where the total Curie count exceeds 27 Curie, where the total Curie count is based upon a sum of all radioactive sources at the facility. Thus, use of larger sources to overcome vessel size limitations may result in an increased need for security at an additional cost.

Accordingly, there exists a need for gamma-ray density gauges that may be used on larger vessels. Additionally, there exists a need for non-contact density gauges that require lower intensity radiation sources. Additionally, there exists a need for non-contact density gauges that can measure the density profile of the fluid in addition to the density at a single location in a vessel.

SUMMARY

In general, in one aspect, embodiments disclosed herein relate to a density profile measuring apparatus including at least one position sensitive gamma ray detector configured to be positioned proximate to the vessel, wherein the position sensitive gamma ray detector is configured to acquire a backscattered gamma ray counts distribution. The position sensitive gamma ray detector is further configured to determine the density profile of the fluid contained in the process vessel based on the backscattered gamma ray counts distribution.

In general, in one aspect, embodiments disclosed herein relate to a method for measuring a density profile of a fluid in a process vessel. The method includes emitting gamma rays into the fluid and acquiring a backscattered gamma ray counts distribution using at least one position sensitive gamma ray detector disposed proximate the vessel. The method further includes determining the density profile of the fluid contained in the process vessel based on the backscattered gamma ray counts distribution, wherein the position sensitive gamma ray detector comprises an ionization detector.

In general, in one aspect, embodiments disclosed herein relate to a density profile measuring apparatus including at least one position sensitive gamma ray detector configured to be positioned proximate to a vessel. The position sensitive gamma ray detector is configured to acquire a backscattered gamma ray counts distribution and determine the density profile of the fluid contained in the process vessel based on the backscattered gamma ray counts distribution. The position sensitive gamma ray detector further includes an ionization detector, including a resistive element, a first output contact connected to a first end of the resistive element and a second output contact connected to a second end of the resistive element, wherein the output contacts are configured to output a first and a second output signal, respectively.

In general, in one aspect, embodiments disclosed herein relate to a process control system for controlling at least one process variable, the system including a memory, a processor operatively connected to the memory, and computer-readable instructions stored in the memory for causing the processor to compute the density profile of the fluid contained in a process vessel. The density profile of the fluid contained in the process vessel is computed based on a backscattered gamma ray counts distribution. The backscattered gamma ray counts distribution is acquired by at least one position sensitive gamma ray detector disposed proximate the vessel.

In general, in one aspect, embodiments disclosed herein relate to a non-transitory computer readable medium including computer-readable instructions for causing a processor to compute a density profile of a fluid contained in a process vessel based on a backscattered gamma ray counts distribution acquired by at least one position sensitive gamma ray detector.

Other aspects and advantages of the invention will be apparent from the following description and the appended claims.

DETAILED DESCRIPTION

In one aspect, embodiments disclosed herein relate to a method for measuring the density profile of a fluid in a vessel using gamma rays. In other aspects, embodiments disclosed herein relate to an apparatus for measuring the density profile of a fluid in a vessel using gamma rays.

As used herein, "backscatter" may refer to the deflection of gamma rays from an original direction. In some embodiments, the backscatter may be isotropic, such as where the gamma rays may be scattered randomly in various directions. Backscattering may occur due to Compton scattering.

As used herein, "fluid" refers to gases, liquids, and solids, or mixtures thereof, that may be contained within a vessel. Fluids may include aqueous liquids, organic liquids, single-phase systems, and multi-phase systems such as foams, emulsions, and fluidized particles. As used herein, "density profile" refers to the density of a fluid at a plurality of locations (i.e., as a function of position). For example, a density profile of a fluid within a vessel may include the density of the fluid at several different positions within the vessel.

Accordingly, as used herein, a position sensitive detector is a detector that is configured to measure a density profile of a fluid in addition to being configured to measure the density, or counts, at a single point. Furthermore, as used herein, a position sensitive detector is a detector configured to measure a plurality of detection events, e.g., backscattered gamma rays, referred to more generally as counts, while also configured to output a signal that indicates the position (absolute or relative) where the gamma ray detection occurred. Furthermore, a position sensitive detector is configured to measure the position of many gamma ray detection events at a plurality, i.e., over a range of positions relative to the position of a fixed detector. In other words, a position sensitive detector is a detector configured to determine the locations of a plurality of detection events.

Figure 1:
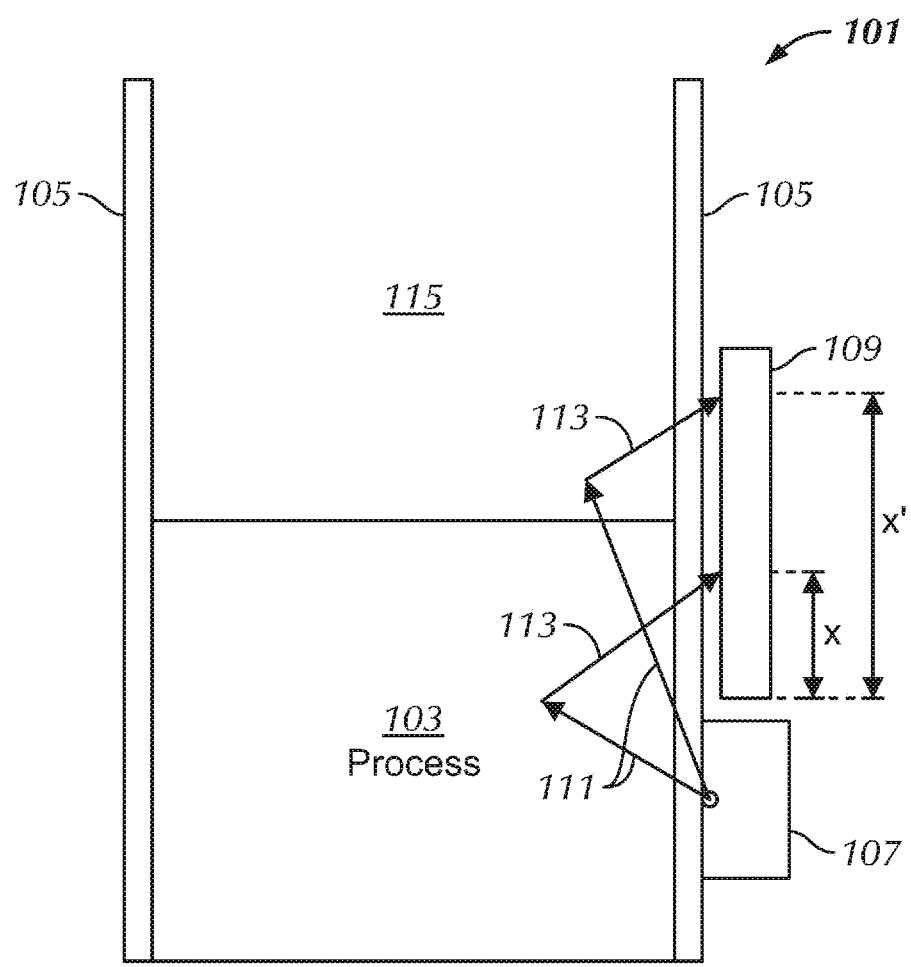
FIG. 1 shows a schematic diagram of a density profile measuring apparatus in accordance with one or more embodiments.

FIG. 1 shows a schematic diagram of a density profile measuring apparatus in accordance with one or more embodiments. The density profile measuring apparatus 101 may be configured to measure the density profile of a process fluid 103 contained within a vessel (not separately shown) having vessel wall 105. The density profile measuring apparatus 101 includes gamma ray source 107 and position sensitive gamma ray detector 109. Both the gamma ray source 107 and the position sensitive gamma ray detector 109 may be attached or otherwise mounted near the wall 105 of the vessel. In accordance with one or more embodiments disclosed herein, the gamma-ray source 107 may emit gamma radiation 111 through the vessel wall 105 and into both the process fluid 103 and into the fluid 115 located above the process fluid 103. The fluid 115 may be, for example, air or vapor from process fluid 103, or any other gases, liquids, and solids, or mixture thereof, associated with the process. The emitted gamma radiation 111 may backscatter from the process fluid 103 and 115, and the backscattered gamma radiation 113 may be subsequently detected at, for example, locations x and x' on the position sensitive gamma ray detector 109. One of ordinary skill will appreciate that the contents of the vessel may be more complex than the simple example shown in FIG. 1. For example, the process fluid 103 may comprise several fluids of differing densities and the fluids may be separated and/or mixed.

Figure 2:
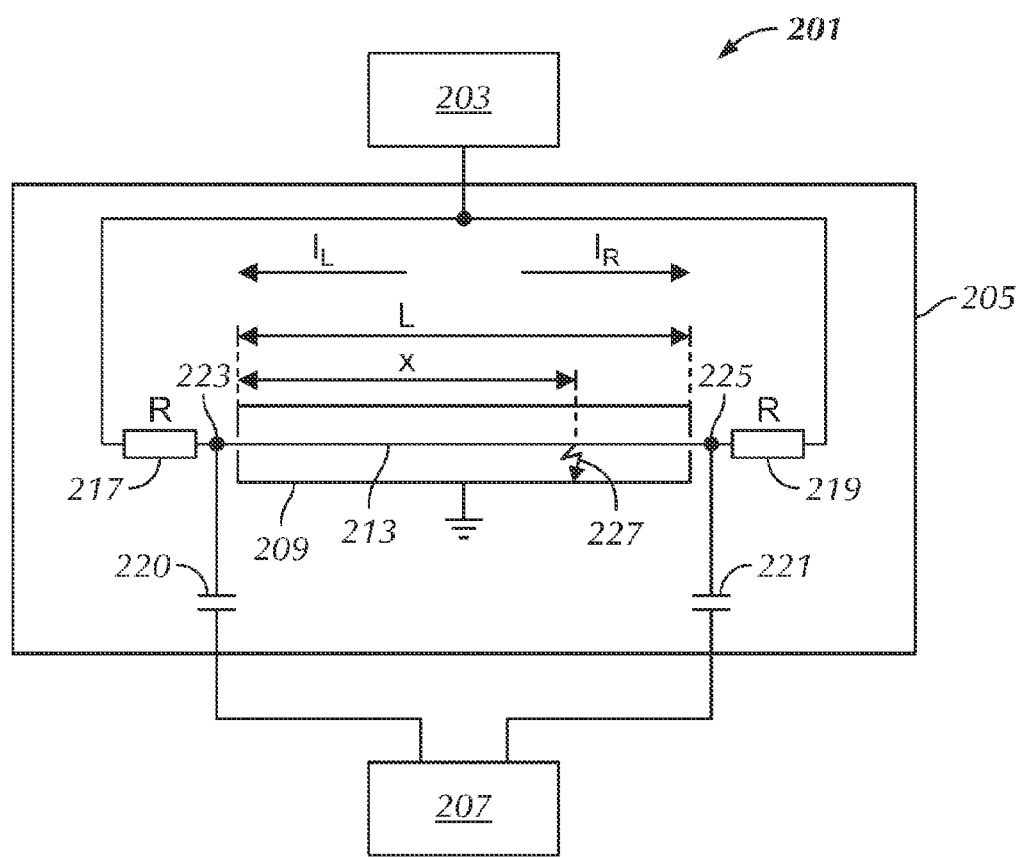
FIG. 2 shows an example of a schematic representation of a position sensitive gamma ray detector in accordance with one or more embodiments.

FIG. 2 shows an example of a schematic representation of a position sensitive gamma ray detector in accordance with one or more embodiments. More specifically, FIG. 2 shows an example of an ionization detector 201 configured as a proportional counter employing a resistive element (e.g., anode wire) configured for charge division readout. Ionization detector 201 may include a voltage source 203, an ionization chamber 205, and a detector electronics module 207. The ionization chamber 205 further comprises a resistive element 213, an electrode 209, load resistors 217, 219, and DC blocking devices 220, 221. Voltage source 203 may be configured to provide a high voltage (for example, in the kV range) to the resistive element 213. The electrode 209 may be held at a low voltage, preferably ground (i.e., 0V). The ionization chamber 205 may be configured to determine the detection position x of a gamma ray along the resistive element 213 by using the peak voltage of two output signals (i.e., output pulses) measured by the detector electronics module 207 at the contacts 223 and 225 located at the resistive element ends, as described below.

In accordance with one or more embodiments, the ionization chamber 205 may be in the shape of a cylinder, with the electrode 209 being of substantially cylindrical shape and with the resistive element 213 placed along the central axis of the cylinder. Voltage source 203 provides a voltage (in the kV range) to the resistive element 213 while the electrode 209 is preferably connected to ground (e.g., 0V). Accordingly, an electric field is directed substantially radially outward from resistive element 213 to the inner surface of the electrode 209. Furthermore, the cylindrical volume bounded by the inner surface of the electrode 209 may be filled with an electrically insulating material, for example Xenon (Xe) gas, or the like. According to one or more embodiments, resistive element 213 may be made from a resistive material, such as Nichrome, Manganin, Constantan, stainless steel, or the like. In accordance with one or more embodiments, the resistivity of the resistive material may range from $5\times10^{-7}$ Ωm to $2\times10^{-6}$ Ωm. However, one of ordinary skill will appreciate that the precise material and resistivity chosen for the resistive element may vary depending on the particular application and design considerations, e.g., sensitivity, stability, cost, etc. Furthermore, load resistors 217 and 219 may be connected between the voltage source 203 and the two contacts 223 and 225, respectively.

In accordance with one or more embodiments, the length of the ionization chamber may be within a range of 6 inches to 6 feet. However, certain applications may call for different lengths that may be outside of this range. Further, in accordance with one or more embodiments, the diameter of the ionization chamber may be within a range of 2 inches to 0.5 inches. However, certain applications may call for different diameters that may be outside of this range.

The operation of the ionization detector 201 in accordance with one or more embodiments is described below with reference to FIG. 2. When an incident gamma ray interacts with the Xe gas, one or more ions are created within the gas. The number of ions created depends on the energy of the incoming gamma ray, with the number of ions created increasing with increasing gamma ray energy. Soon after ionization occurs, the ions move in response to the electric field located within the ionization chamber, with the positive and negative ions pulled in opposite directions toward oppositely charged electrodes. The ions are eventually neutralized at the electrode 209 and the resistive element 213, thereby creating an ion current that is directly proportional to the number of ions transferred to the electrodes.

Thus, the ionization in the Xe gas due to the scattering of a gamma ray from Xe atoms creates a temporary conductive path 227 that connects the electrode 209 and the resistive element 213 at the location of ionization of the gamma ray. Accordingly, there are two paths for the ion current (i.e., the output signal) to flow to ground. Because these two paths are connected in parallel, the magnitude of the ion current in each path is inversely proportional to the total resistance of the respective path. The first output signal path carries a current $I_L$ that is inversely proportional to the total resistance of the first path, given by R+ρ(x/L), where ρ is the total resistance of the resistive element 213, L is the total length of the resistive element 213, x is the position of the gamma ray induced ionization as measured from one end of the resistive element 213, and R is the resistance of load resistors 217 and 219. The second output signal path carries a current $I_R$ that is inversely proportional to the total resistance of second path, given by R+ρ(1−x/L). Accordingly, the position x of the gamma ray detection may be determined based on a comparison of the two voltages present at the two contacts 223 and 225. For example, the ratio between the two voltages present at the two contacts 223 and 225 is given by:

$$\frac{V_R}{V_L} = \frac{R + \left(\frac{x}{L}\right)\rho}{R + \left(1 - \frac{x}{L}\right)\rho} \quad (2)$$

where $V_L$ is the voltage measured at contact 223 and $V_R$ is the voltage measured the contact 225. More specifically, because of the transient nature of the gamma ray induced ionization, $V_L$ and $V_R$ may be more properly interpreted as the peak amplitudes of the output signals (i.e., output pulses) measured by the detector electronics module 207 at the contacts 223 and 225. Equation (2) may be inverted to yield the detection location of the gamma ray:

$$x = L\frac{V_R\left(\frac{R}{\rho} + 1\right) - V_L\frac{R}{\rho}}{V_L + V_R} \quad (3)$$

Thus, if R and ρ are both known, x may be determined through a measurement of both $V_R$ and $V_L$. In accordance with one or more embodiments disclosed herein, the resistance p of the resistive element 213 may be equal or comparable to the resistance R of the load resistors 217 and 219. For example, in the case where ρ=R, Eq. (3) reduces to:

$$x = L\frac{2V_R - V_L}{V_L + V_R} \quad (4)$$

Accordingly, measurement of the voltages $V_R$ and $V_L$ allow for the determination the position x of the gamma ray detection. One of ordinary skill having the benefit of this disclosure will appreciate that other comparisons of the voltages may be used to derive a position sensitive signal. Accordingly, Eq. (4) is understood to be one example of a possible useful comparison.

Figure 3:
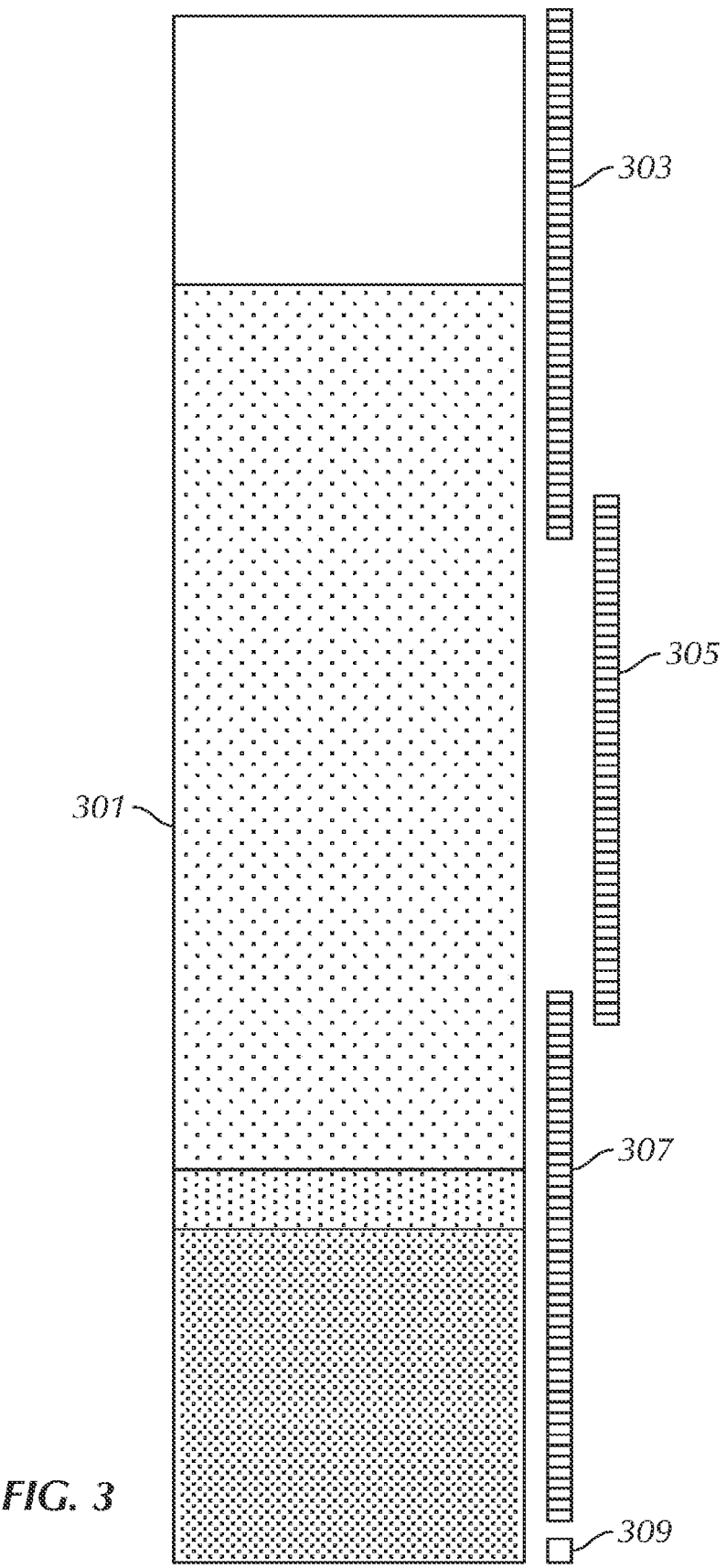
FIG. 3 shows a schematic diagram of a density profile measuring apparatus in accordance with one or more embodiments.

FIG. 3 shows a schematic diagram of a density profile measuring apparatus in accordance with one or more embodiments. In a situation where the vessel 301 is very long or tall, several position sensitive gamma ray detectors (e.g., detectors 303, 305, and 307) may be placed along the length or height of the vessel 301, with one or more gamma ray sources 309 also placed along the vessel. The placement of several shorter individual position sensitive detectors allows for improved thermal and vibrational properties. For example, the systematic changes in detector calibration associated with the thermal expansion/contraction of the resistive element and/or the thermal expansion/contraction of the ionization chamber housing may be reduced by reducing the overall length of the resistive element and ionization chamber housing. The length of the gamma ray detector may also be chosen to minimize efficient coupling of the vibrational frequencies that may be prevalent in the environment near the detector. While FIG. 3 shows the ends of the position sensitive detectors as partially overlapped, one of ordinary skill will appreciate that other configurations are possible without departing form the scope of the present disclosure. For example, in accordance with another embodiment, the position sensitive detectors may be placed end-to-end. In addition, one of ordinary skill will appreciate that the particular demands of a given detector environment may require any number of detectors having a particular length or number of gamma ray sources. Accordingly, FIG. 3 is meant to provide an illustrative example and is not meant to limit the scope of the present disclosure.

The gamma-ray sources 107 (of FIG. 1) and 309 (of FIG. 3) may include, for example, cesium-137, americium-241, radium-226, iridium-192, and cobalt-60, or any other suitable radioactive source. In some embodiments, the activity of the source may range from 0.1 mCi to 10 Ci. In other embodiments, the activity of the source may be less than 5 Ci; less than 2 Ci in other embodiments; and less than 1 Ci in yet other embodiments.

Figure 4A:
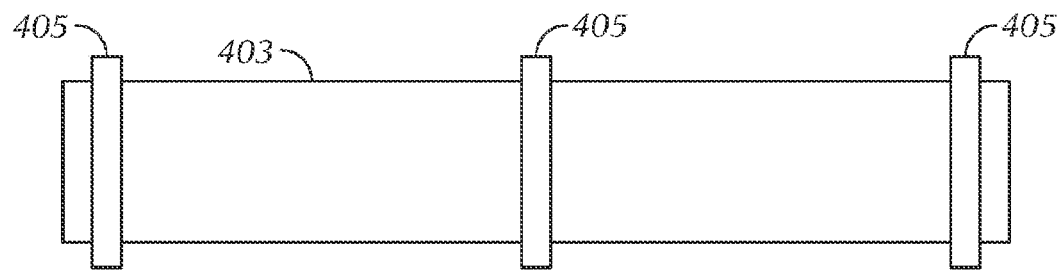
FIG. 4A-B show how a position sensitive gamma ray detector may be mounted to a vessel in accordance with one or more embodiments.
Figure 4B:
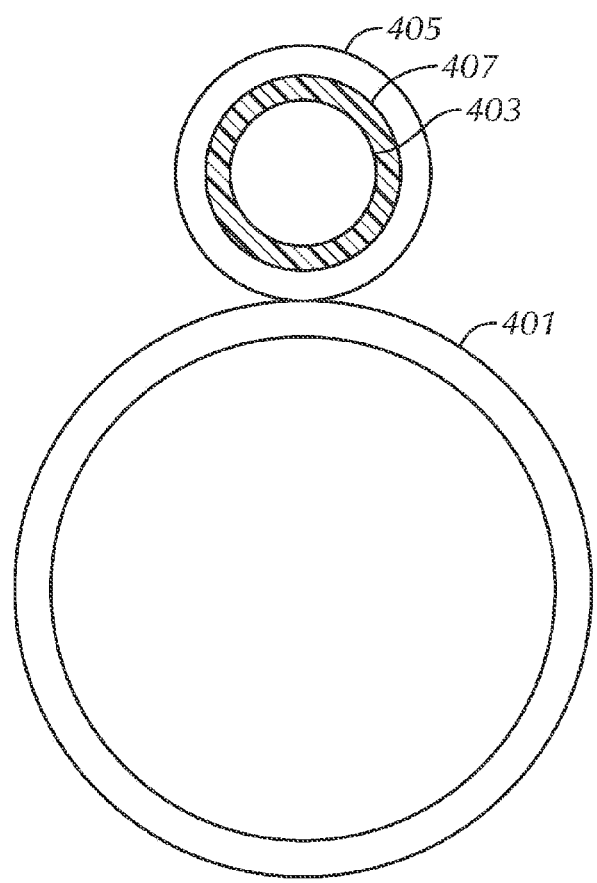

FIGS. 4A-B show how a position sensitive gamma ray detector may be mounted to a vessel in accordance with one or more embodiments disclosed herein. The position sensitive gamma ray detector 403 may be mounted to a vessel 401 by means of a mounting adaptor 405. The mounting adapter 405 may be rigidly attached to the vessel 401, by any method commonly known in the art, for example, by welding. Many industrial applications produce significant vibrations which may transmit through the mounting adaptors into the position sensitive gamma ray detector 403. This vibration can induce electrical noise by creating capacitance changes in the detection elements, which in turn creates noise in the system otherwise known as microphonics. Depending on the configuration of the position sensitive gamma ray detector 403, the noise can be in the frequency range of 10 kHz or more. The use of mechanical dampeners as part of the support systems helps to reduce these effects. The dampening system includes a bushing 407 formed from an elastomeric material. Bushing 407 may be disposed between the mounting adapter 405 and the position sensitive gamma ray detector 403. The quantity and position of the adapters may vary according to different configurations of the detectors. The bushing 407 not only reduces the microphonic noise, but also provides a thermal barrier between the detector and the vessel.

Figure 5:
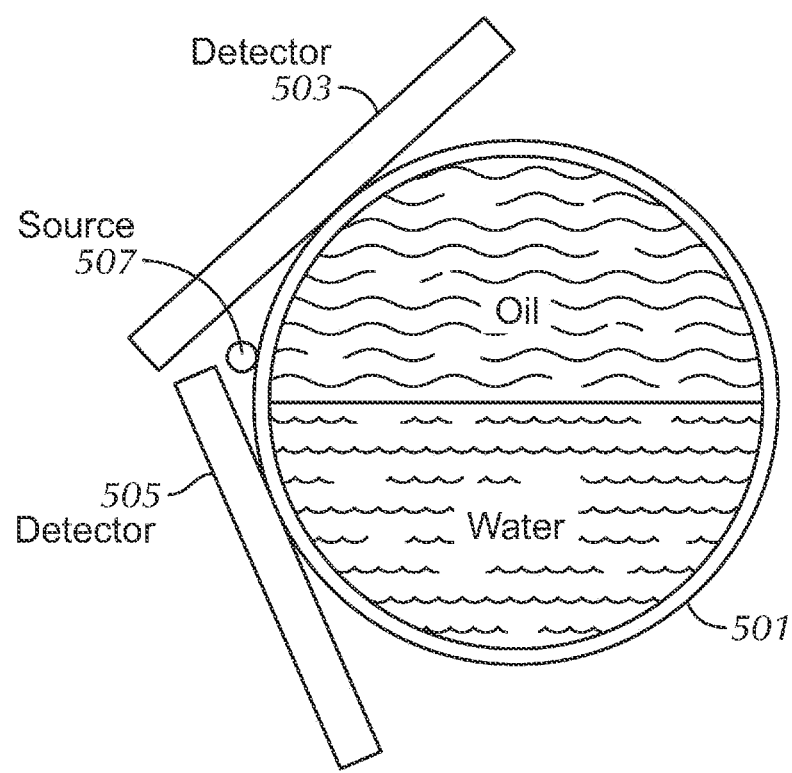
FIG. 5 shows how a position sensitive gamma ray detector may be mounted to a vessel in accordance with one or more embodiments.

FIG. 5 shows position sensitive gamma ray detectors mounted to a vessel in accordance with one or more embodiments disclosed herein. In this example, the cross section of the vessel 501 is shown as circular, as would be the case for a cylindrical vessel mounted horizontally, i.e. parallel to the ground. Further, in accordance with one or more embodiments of the invention, many different types of vessels having different cross-sectional shapes may be used without departing from the scope of the present disclosure. In accordance with one or more embodiments, position sensitive detectors 503 and 505 may be mounted such that they may measure the density profile of the fluid in the cross sectional direction (e.g., perpendicular to the symmetry axis) of vessel 501. In accordance with one or more embodiments, a gamma ray source 507 may be mounted on or near the vessel and the position sensitive detectors.

While a cylindrically shaped ion chamber is shown in FIGS. 4A-B, one of ordinary skill in the art will appreciate that various shapes of the ion chamber may be used without departing from the scope of the present disclosure. For example, the ion chamber may be box-shaped, which may include a pair of parallel plates or any other convenient geometry.

One of ordinary skill will appreciate that the position sensitive detector may be alternatively configured in many ways and is not necessarily limited to the proportional counter described in detail above.

Figure 6:
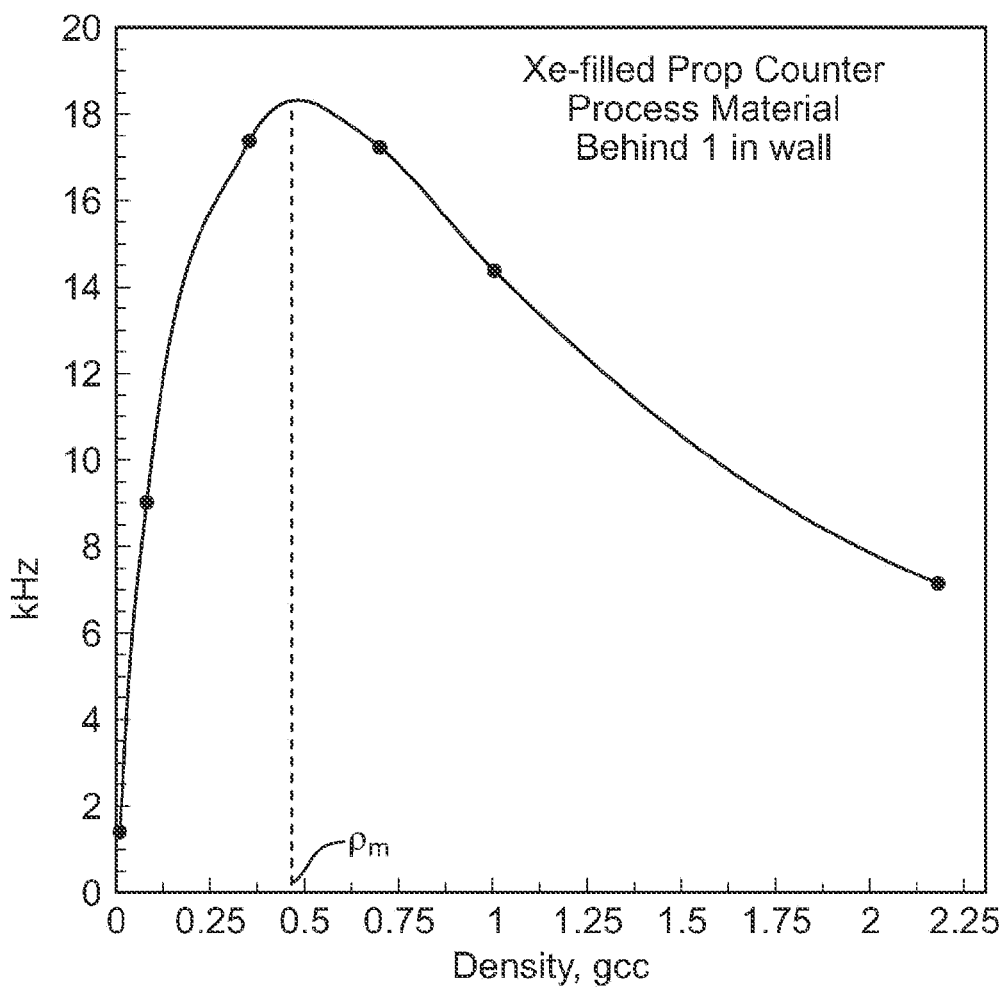
FIG. 6 shows a calibration curve for a backscattered gamma ray detector in accordance with one or more embodiments.

FIG. 6 shows an example of an empirical chart depicting the counting rate of backscattered gamma rays as a function of density of a process fluid in accordance with embodiments disclosed herein. In this illustrative embodiment, the counting rate as a function of density is shown for a Xe-filled proportional counter mounted to a vessel having a 1 inch thick vessel wall. As can be seen from FIG. 6, a density of 0.120 gcc (grams per cubic centimeter) may produce the same count rate as that of a density of 2.20 gcc. Therefore, the operational range may be divided into two regions, as described below.

The peak counting rate is indicated by $\rho_m$. One or more embodiments disclosed herein may operate within a region where the density $\rho < \rho_m$, e.g., densities located to the left of the maximum of the curve in FIG. 6. Similarly, one or more embodiments disclosed herein may operate within a high density region, $\rho < \rho_m$, represented by densities located to the right of the maximum of the curve in FIG. 6. Specifically, in many industrial applications, for example, in many refineries, the fluid may be mostly oil having a density of 0.8 gcc or higher. As a further example, industrial applications in mining fluids may be mostly water having a density of 1.0 gcc or higher.

The ability to measure the back scattered gamma rays may depend on many factors, including but not limited to, the density of the fluid, vessel wall thickness, source-detector distance, source intensity, etc. Accordingly, the dependence of the count rate on the fluid density will vary with the specific operational conditions. Thus, FIG. 6 is meant to provide an illustrative example and is not meant to limit the scope of the present disclosure.

Figure 7A:
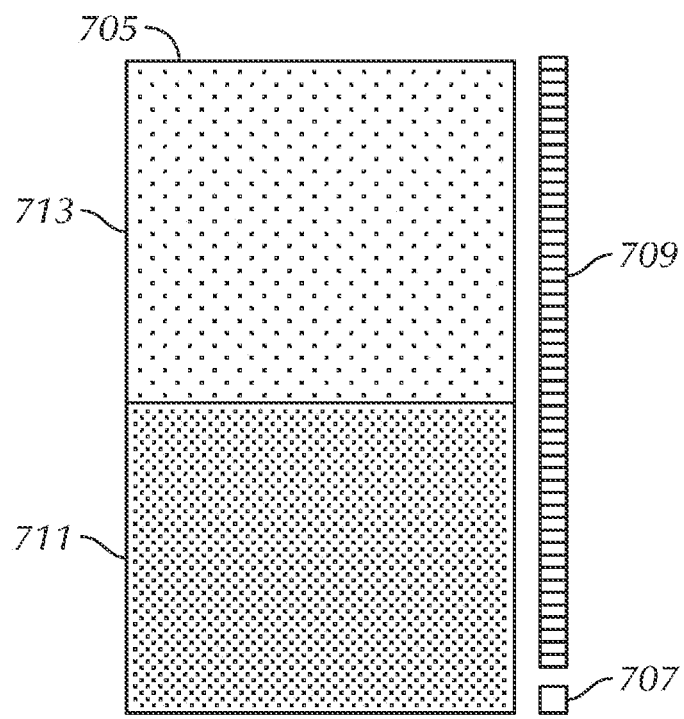
FIG. 7A shows a schematic diagram of a density profile measuring apparatus in accordance with one or more embodiments.

FIG. 7A shows a schematic diagram of a density profile measuring apparatus in accordance with one or more embodiments. Vessel 705 may be filled with a mixture of fluids where each fluid has a different density. In the example shown in FIG. 7A, the vessel 705 is filled partially with fluid 711 (e.g., 0.45 gcc froth) and partially with fluid 713 (e.g., 0.0012 gcc air). A gamma ray source 707 and a position sensitive gamma ray detector 709 are both attached or otherwise mounted near the wall of the vessel 705. In accordance with one or more embodiments disclosed herein, the position sensitive gamma ray detector 709 may be used to determine the interface between fluids 711 and 713 and to determine the densities of fluid 711 and 713.

Figure 7B:
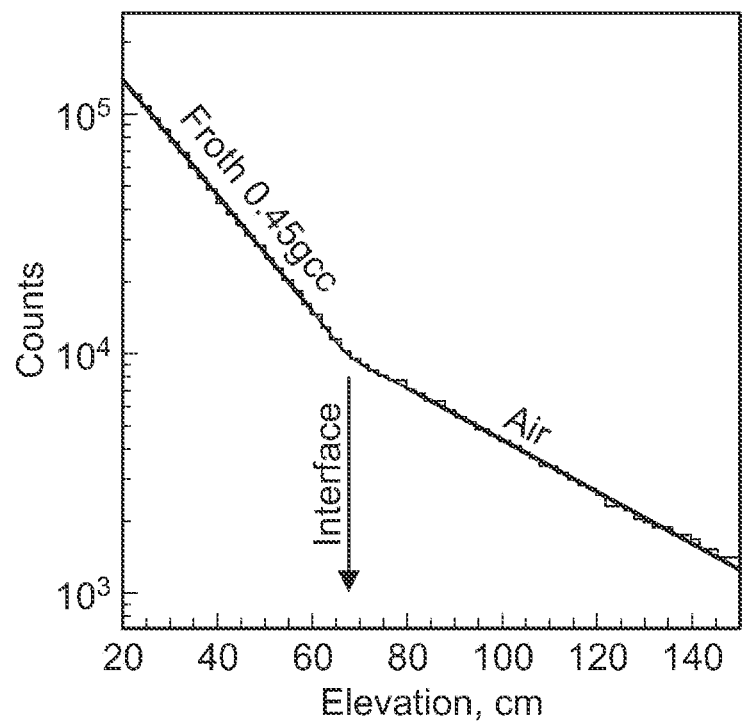
FIG. 7B shows a simulated response of a position sensitive detector in accordance with one or more embodiments.

FIG. 7B shows a simulated response of a position sensitive detector in accordance with one or more embodiments disclosed herein. In this example, a Monte Carlo simulation of Compton scattering of the gamma rays is performed and returns the count rate on the detector for an input fluid. Specifically, FIG. 7B shows a semi-log plot of a backscattered gamma ray counts distribution on the position sensitive detector 709. As used herein, the backscattered gamma ray counts distribution is defined as the spatial distribution of total counts as measured on the detector over a time interval dt. Furthermore, it will be assumed that the backscattered gamma ray counts distribution is equivalent to the count-rate distribution, where the count-rate is simply given by the number of counts N divided by the measurement time dt. FIG. 7B shows that, on a semi-log plot, the backscattered gamma ray counts distribution for a fluid with a constant density is described well by a linear relationship having a decreasing slope m, or:

$$m = \frac{d}{dx}\log(N) = -\alpha\rho + \beta \quad (5)$$

where $\alpha$ and $\beta$ are a calibration factors, and $\rho$ is the density of the fluid. The calibration constants may depend on many factors, including but not limited to, vessel wall thickness, source-detector distance, source intensity, and ion chamber design (e.g., geometry and gas type). However, $\alpha$ and $\beta$ may be determined by calibrating the system with any two calibration fluids that possess a known density, for example, air and water.

FIG. 7B further shows that the interface between the 0.45 gcc froth and water may be identified as a discontinuity, or kink, in the slope of the backscattered gamma ray counts distribution when plotted on a semilog plot. Thus, the interface can be located without prior knowledge of the calibration constant $\alpha$. Furthermore, the linear backscattered gamma ray counts distribution on the semi-log plot shown in FIG. 7B implies that for a fixed density, the number of counts, as measured on the position sensitive detector, decays exponentially with increasing elevation from the gamma ray source.

In the demanding environments associated with many industrial processes it may become difficult to accurately determine the position of a gamma ray detection event according to Eq. (2). For example, noise sources that couple to, for example, the output signals $V_L$ and $V_R$ lead to the existence of a minimum position sensitivity $\delta x$. Furthermore, due to the random, i.e., statistical nature of the physical process of gamma ray backscattering, the fractional uncertainty in the measured number of counts scales as one over the square root of the number of counts, or % $\delta N/N \propto 1/\sqrt{N}$. Thus, it may become useful to employ a binning technique to reduce noise and/or statistical uncertainty and to improve data acquisition time by increasing the number of counts obtained for any given data acquisition event occurring over a time dt. For example, the position sensitive detector may be effectively split into a number of virtual subdetectors of size $\delta x$ or larger and all detections that fall within any given virtual subdetector width may be summed to reduce error in the counts.

Thus, in accordance with one or more embodiments, even though the position sensitive detector may be a single unit (for example, FIG. 4), the data output from the detector may be processed as if the position sensitive detector comprised several smaller virtual subdetectors each having a width w. The smaller the virtual subdetector divisions, the more subdetectors are available, thus increasing the spatial resolution of the measurement. Larger virtual subdetector divisions provides for fewer virtual subdetectors and, thus, lower spatial resolution. However, larger subdetector divisions provide for a higher number of counts collected at each virtual subdetector, thus, increasing the precision in the density measurement.

The virtual subdetector divisions can also be understood in the context of Eq. (3). For example, counts detected at a position $x_i \pm w/2$ may be summed together, or binned. The next virtual subdetector consist of all counts located at the position $(x_i + w) \pm w/2$. Thus the nth virtual subdetector comprises all of the counts measured within the range $(x_i + nw) \pm w/2$.

In accordance with one or more embodiments, the density at a position x along the length or height of the vessel may be measured. For example, if the whole system is calibrated the measurement of the density $\rho$ between two adjacent subdetectors numbered i and i+1 can be inferred from the difference in counts between the two subdectors (i.e., the slope of the backscattered gamma ray counts distribution):

$$\rho = \alpha \frac{\log N_{i+1} - \log N_i}{x_{i+1} - x_i} \quad (6)$$

Figure 8A:
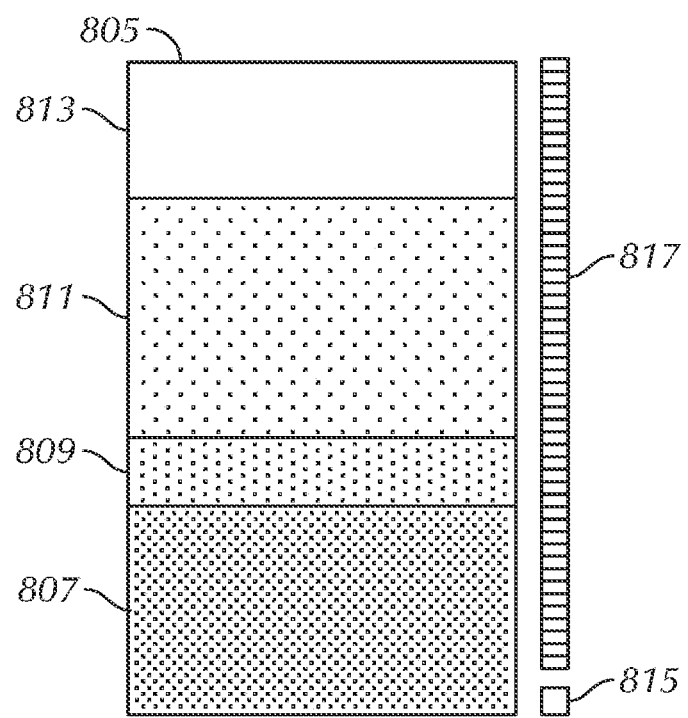
FIG. 8A shows a schematic diagram of a density profile measuring apparatus in accordance with one or more embodiments.

FIG. 8A shows a schematic diagram of a density profile measuring apparatus in accordance with one or more embodiments. Vessel 805 may be filled with a mixture of fluids wherein each fluid may have a different density or each fluid my have a nonuniform density profile. In the example shown in FIG. 8A, the vessel 805 is filled partially with fluids 807, 809, 811, 813. A gamma ray source 815 and a position sensitive gamma ray detector 817 are both attached or otherwise mounted near the wall of the vessel 805. In accordance with one or more embodiments disclosed herein, the position sensitive gamma ray detector 817 may be used to determine the interface between the various fluids in addition to the density distributions of all the fluids according to Eq. (6).

Figure 8B:
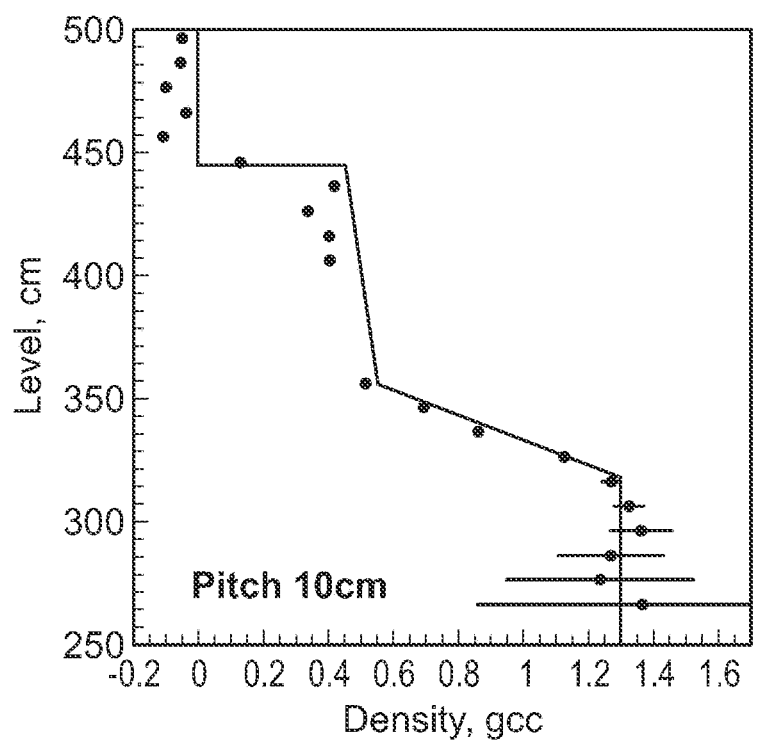
FIG. 8B-C show simulated responses of a position sensitive detector in accordance with one or more embodiments.
Figure 8C:
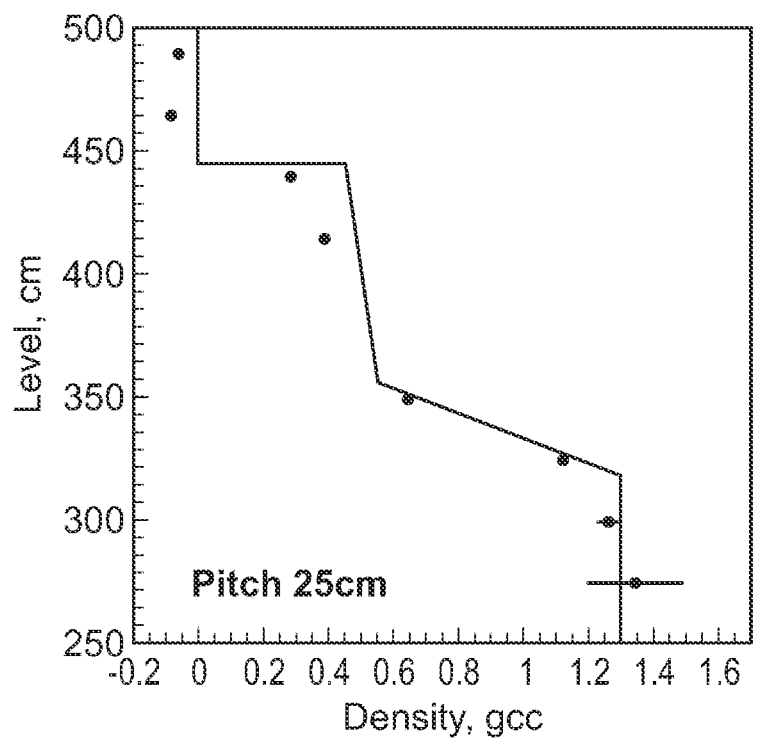

FIG. 8B-C show simulated responses of a position sensitive detector in accordance with one or more embodiments disclosed herein, wherein a Monte Carlo simulation of the Compton scattering of the gamma rays is performed. Assuming each virtual subdetector is calibrated, the density between each virtual subdetector can be inferred from the measured counts on each virtual subdetector according to Eq. (6).

The solid lines show the input density profile of the fluid that was used in simulation. In this example, fluid 807 was simulated with a constant density, fluids 809 and 811 were simulated with linear density profiles, and fluid 813 was simulated as empty space (0 gcc). The individual data points show the results from the simulation. FIG. 8B, shows the results from a simulation in which the detector was subdivided into virtual subdetectors each having a 10 cm width. FIG. 8C, shows the results of a simulation wherein the detector was subdivided into virtual subdetectors each having a 30 cm width. Both configuration of virtual subdetectors are seen to provide an accurate reconstruction of the simulated density profile.

Figure 9:
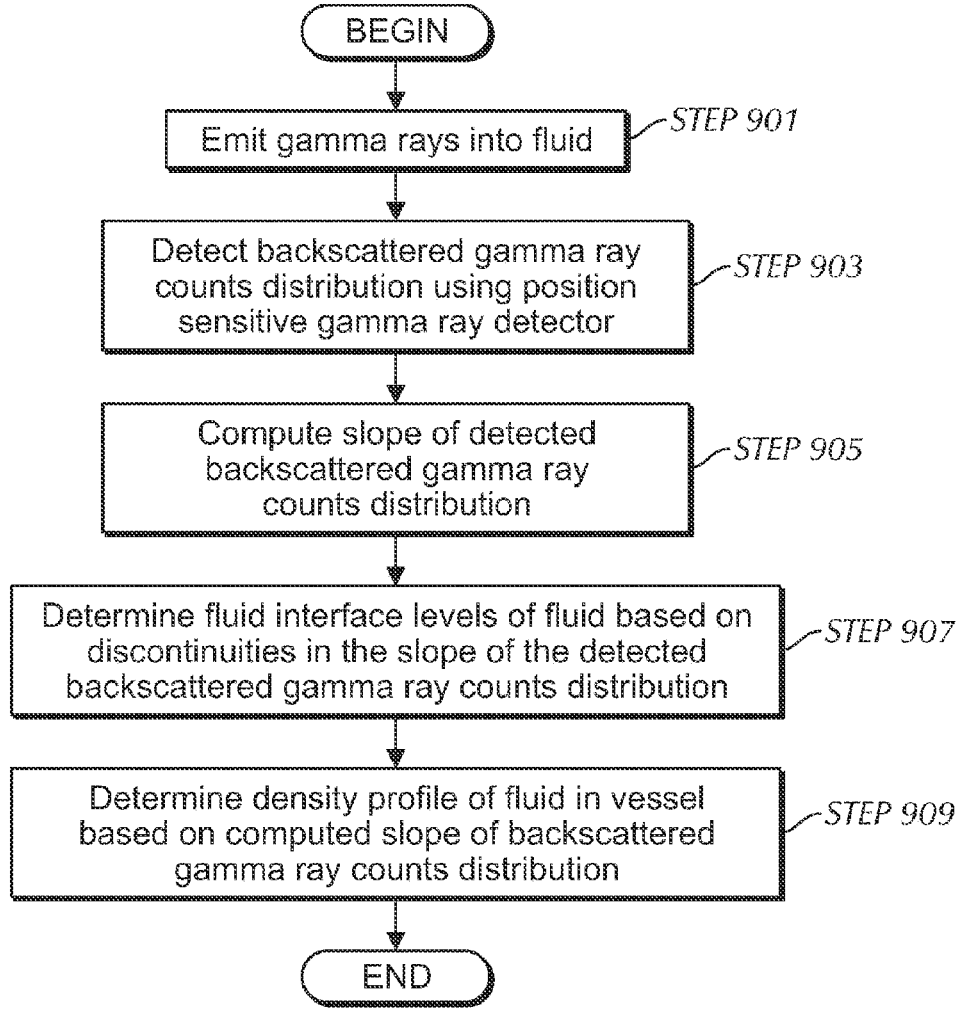
FIG. 9 shows a flow chart in accordance with one or more embodiments.

FIG. 9 shows a method illustrating the steps involved in measuring a density profile of a fluid in a process vessel in accordance with one or more embodiments. While the various steps in the flowchart are presented and described sequentially, one of ordinary skill will appreciate that some or all of the steps may be executed in different orders, may be combined, or omitted, and some or all of the steps may be executed in parallel.

In step 901, gamma rays are emitted into the fluid. These gamma rays may originate from a suitable gamma ray source positioned outside of the process vessel, as shown above, for example, in FIGS. 1, 3, 7A, and 8A. In step 903, a backscattered gamma ray counts distribution (BGCD) is detected by a position sensitive gamma ray detector. One example of a BGCD detected by a position sensitive gamma ray detector is shown in FIG. 7B. In accordance with one or more embodiments of the invention, the position sensitive gamma ray detector may be configured as a proportional counter employing charge division readout, as described above in reference to FIG. 2. However, one of ordinary skill having the benefit of the present disclosure will appreciate that any suitable type of position sensitive detector may be used without departing from the scope of the present disclosure, e.g., plastic scintillators, etc. In step 905, the slope of the BGCD is computed at one or more detection positions along the process vessel. In accordance with one or more embodiments, the slope of the BGCD may be computed for a plurality of positions along the gamma ray counts distribution according to Eq. (6). It should be noted that for step 905, the calibration factor $\alpha$, shown in Eq. (6), need not be known to determine the slope of the BGCD. In step 907, the level (i.e., position, height, etc.) of an interface between two fluids may be determined based on the presence of any discontinuities in the slope of the BGCD. For example, FIG. 7B illustrates an interface located between fluid 711 and 713, the interface being recognizable as the discontinuity in the slope of the BGCD. In step 909, the density profile of the fluid may be determined based on the computed slope of the BGCD using Eq. (6) and the predetermined values of the necessary calibration constants, e.g., $\alpha$, $\beta$ and/or any other necessary offset/calibration values, etc.

Gamma-ray backscatter density meters, in accordance with embodiments disclosed herein, may measure the density of a fluid in a vessel, where the density of the fluid may range from 0 gcc to 7.0 gcc. The effective density range may be from 0.1 gcc to 4.0 gcc in other embodiments; and from 0.2 to 2.0 gcc in yet other embodiments. In other embodiments, one or more position sensitive gamma-ray detectors may be used in conjunction with one or more gamma-ray through-transmission density meters.

Advantageously, the methods and apparatus disclosed herein may be used to measure density profiles of fluids in a vessel, or to locate one or more interfaces between multiple fluids in a process vessel. The measured density profiles may, for example, provide an indication of the degree of settling or mixing that may be occurring in a vessel. In addition, a vertical density profile may indicate the degree of settling of a solid from a suspension contained within a vessel. As another example, various density profiles may be indicative of static, laminar, or turbulent flow in a vessel. Where vessels form a component in a process, one or more process variables may be manipulated in response to the density profile, such as to increase mixing or to decrease settling rates. Where one or more interfaces between fluids is detected, one or more process variables may be manipulated to alter the level of the interface between process fluids (i.e., the process level) within the process vessel.

In other various embodiments, the density and/or density profile of a fluid in a vessel (i.e., the process density and/or process density profile) may be controlled by manipulating one or more process variables based upon the measured density and/or density profile. For example, where a vessel forms a component in a process, one or more process variables may be manipulated in response to the position sensitive gamma-ray backscatter density measurement of the fluid in the vessel.

Figure 10:
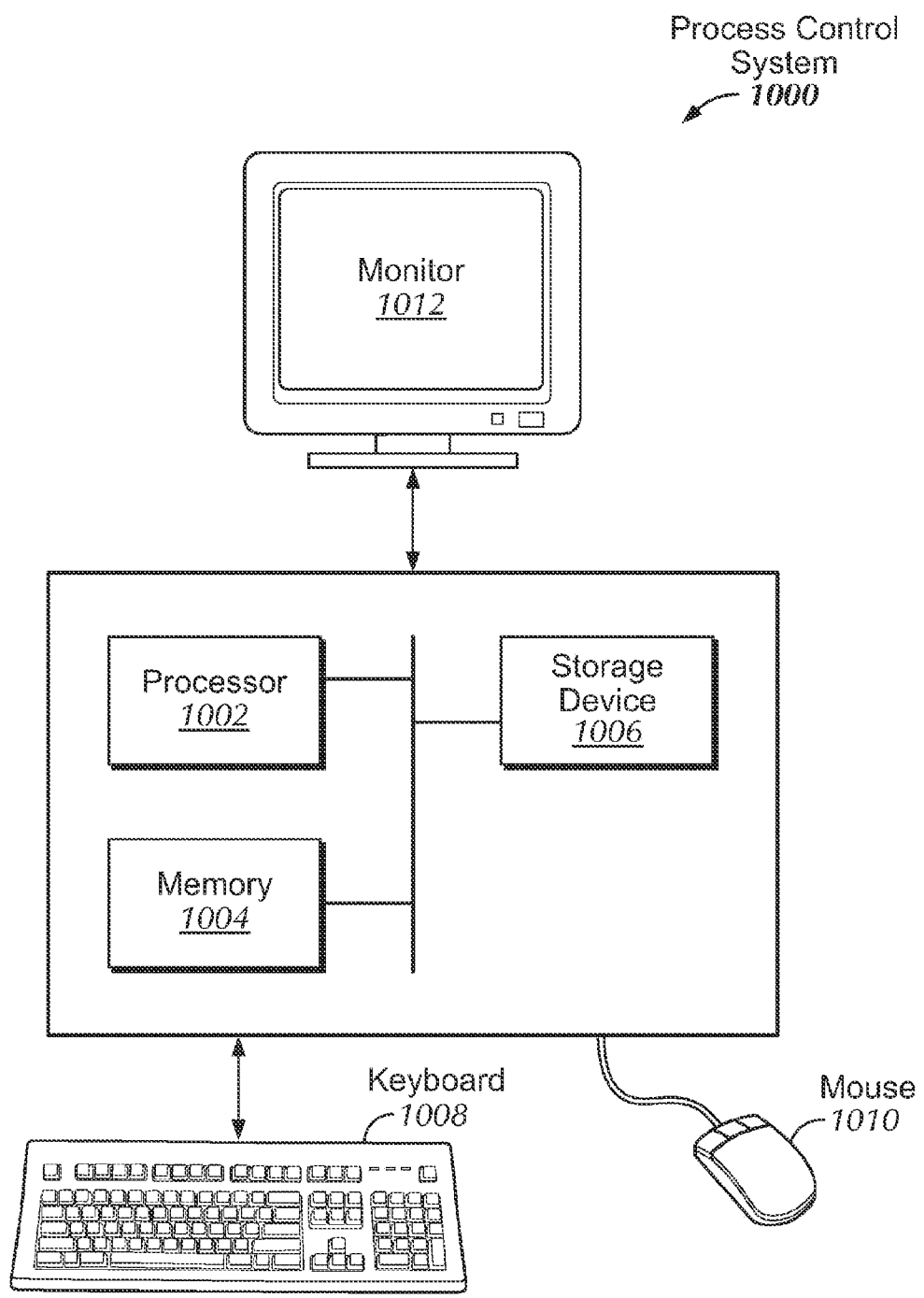
FIG. 10 shows a system in accordance with one or more embodiments.

Further, one or more embodiments disclosed herein may be implemented on any type of computer system such as a process control system. For example, as shown in FIG. 10, a process control system 1000 includes a processor 1002, associated memory 1004, a storage device 1006, and numerous other elements and functionalities typical of today's computers (not shown). The memory 1004 may include instructions for causing the process control system 1000 to perform a process control method in accordance with one or more embodiments of the present disclosure.

The process control system 1000 may also include input means, such as a keyboard 1008 and a mouse 1010, and output means, such as a monitor 1012. The process control system 1000 may be connected to a local area network (LAN) or a wide area network (e.g., the Internet) (not shown) via a network interface connection (not shown). Those skilled in the art will appreciate that these input and output means may take other forms, now known or later developed.

Further, those skilled in the art will appreciate that one or more elements of the process control system 1000 may be located at a remote location and connected to the other elements over a network. Further, one or more embodiments may be implemented on a distributed system having a plurality of nodes, where each portion of the invention (e.g., intrusion detection system, response rewriter, server, client) may be located on a different node within the distributed system. In one or more embodiments, the node corresponds to a computer system. Alternatively, the node may correspond to a processor with associated physical memory. The node may alternatively correspond to a processor with shared memory and/or resources. Further, software instructions to perform embodiments of the invention may be stored on a tangible computer readable medium such as a digital video disc (DVD), compact disc (CD), a diskette, a tape, or any other suitable tangible computer-readable storage device.

Advantageously, embodiments disclosed herein may provide for a method of making non-contact density profile measurements by positioning a position sensitive gamma-ray detector relative to a gamma-ray source so as to detect gamma-ray backscatter. The non-contact measurement may allow for the measurement of the density profile of material in a vessel, where the material is hazardous, extremely hot, or where direct contact measurements are not possible. By detecting gamma-ray backscatter, gamma rays do not have to traverse the entire vessel diameter, which may allow for the use of lower intensity gamma-ray sources as well as measurement of density profile in larger vessels than is currently possible with through-transmission measurements.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A density profile measuring apparatus comprising:
   at least one position sensitive gamma ray detector configured to be positioned proximate to a process vessel, wherein the position sensitive gamma ray detector is configured to acquire a backscattered gamma ray counts distribution and wherein the density profile measuring apparatus is configured to determine the density profile of a fluid contained in the process vessel based on the backscattered gamma ray counts distribution;
   wherein the position sensitive gamma ray detector comprises an ionization detector comprising:
      a resistive element;
      a first output contact connected to a first end of the resistive element,
      a second output contact connected to a second end of the resistive element,
      wherein the first output contact and second output contact are configured to output a first and a second output signal, respectively.

2. The density profile measuring apparatus of claim 1, further comprising at least one gamma ray source configured to emit gamma rays into the fluid.

3. The density profile measuring apparatus of claim 1, wherein the ionization detector is filled with an electrically insulating material.

4. The density profile measuring apparatus of claim 1, wherein the ionization detector is configured to operate as a position sensitive proportional counter.

5. The density profile measuring apparatus of claim 1, wherein the position sensitive gamma ray detector is configured to employ charge division readout.

6. The density profile apparatus of claim 1, further comprising:
a detector electronics module configured to determine a detection position of a backscattered gamma ray based on a comparison of a first output signal and a second output signal,
wherein the first output signal is output from the first contact and the second output signal is output from the second contact.

7. The density profile apparatus of claim 6, wherein the electronics module is further configured to determine the detection position based on the formula $$x = L\frac{V_R\left(\frac{R}{\rho}+1\right)-V_L\frac{R}{\rho}}{V_L+V_R}.$$

8. The density profile apparatus of claim 6, wherein the detector electronics module is further configured to measure the fluid density at a location in the vessel by computing a slope of the backscattered gamma ray counts distribution at the detection position.

9. A method for measuring a density profile of a fluid in a process vessel comprising:
emitting gamma rays into the fluid; and
acquiring a backscattered gamma ray counts distribution using at least one position sensitive gamma ray detector disposed proximate the vessel,
determining the density profile of the fluid contained in the process vessel based on the backscattered gamma ray counts distribution,
wherein the position sensitive gamma ray detector comprises an ionization detector comprising:
a resistive element;
a first output contact connected to a first end of the resistive element; and
a second output contact connected to a second end of the resistive element, wherein the output contacts are configured to output a first and a second output signal, respectively.

10. The method of claim 9, wherein acquiring a backscattered gamma ray counts distribution further comprises determining a detection position of a backscattered gamma ray based on a comparison of a first and a second output signal, wherein the first output signal is output from the first output contact and the second output signal is output from the second output contact.

11. The method of claim 9, wherein determining the detection position of the backscattered gamma ray using the first and second output signals is made according to the formula $$x = L\frac{V_R\left(\frac{R}{\rho}+1\right)-V_L\frac{R}{\rho}}{V_L+V_R}.$$

12. The method of claim 9 wherein determining the density profile further comprises computing a slope of the measured backscattered gamma ray counts distribution at the detection position.

13. A density profile measuring apparatus comprising:
at least one position sensitive gamma ray detector configured to be positioned proximate to a vessel,
wherein the position sensitive gamma ray detector is configured to acquire a backscattered gamma ray counts distribution and determine the density profile of the fluid contained in the process vessel based on the backscattered gamma ray counts distribution,
wherein the position sensitive gamma ray detector further comprises:
an ionization detector, comprising:
a resistive element;
a first output contact connected to a first end of the resistive element and a second output contact connected to a second end of the resistive element, wherein the output contacts are configured to output a first and a second output signal, respectively.

14. The density profile measuring apparatus of claim 13, further comprising: a detector electronics module configured to determine a detection position of a backscattered gamma ray using a relationship between the first and the second output signals.

15. A process control system for controlling at least one process variable, the system comprising:
a memory;
a processor operatively connected to the memory; and
computer-readable instructions stored in the memory for causing the processor to compute a density profile of a fluid contained in a process vessel based on a backscattered gamma ray counts distribution acquired by at least one position sensitive gamma ray detector disposed proximate the vessel;
wherein the position sensitive gamma ray detector comprises an ionization detector comprising:
a resistive element;
a first output contact connected to a first end of the resistive element;
a second output contact connected to a second end of the resistive element,
wherein the first output contact and second output contact are configured to output a first and a second output signal, respectively.

16. The process control system of claim 15, further comprising computer-readable instructions stored in the memory for causing the processor to change the at least one process variable based on the computed density profile.

17. The process control system of claim 16, wherein the process variable is at least one of process density, process level, and process density profile.

18. A non-transitory computer readable medium comprising computer-readable instructions for causing a processor to compute a density profile of a fluid contained in a process vessel based on a backscattered gamma ray counts distribution acquired by at least one position sensitive gamma ray detector,
wherein the position sensitive gamma ray detector comprises an ionization detector comprising:
a resistive element;
a first output contact connected to a first end of the resistive element;
a second output contact connected to a second end of the resistive element,
wherein the first output contact and second output contact are configured to output a first and a second output signal, respectively.

* * * * *

UNITED STATES PATENT AND TRADEMARK OFFICE
CERTIFICATE OF CORRECTION

PATENT NO. : 8,983,028 B2  
APPLICATION NO. : 13/298155  
DATED : March 17, 2015  
INVENTOR(S) : Kulik et al.

Page 1 of 1

It is certified that error appears in the above-identified patent and that said Letters Patent is hereby corrected as shown below:

In the claims

Column 12, line 56 In Claim 1, delete "element," and insert -- element; and --, therefor.

Column 13, line 54 In Claim 11, delete "claim 9," and insert -- claim 10, --, therefor.

Column 13, line 64 In Claim 12, delete "claim 9" and insert -- claim 10 --, therefor.

Signed and Sealed this
Sixteenth Day of August, 2016

Michelle K. Lee
*Director of the United States Patent and Trademark Office*